United States Patent [19]

Renge et al.

[11] Patent Number: 4,990,697
[45] Date of Patent: Feb. 5, 1991

[54] PROCESS FOR PRODUCING HOMOALLYL ALCOHOLS

[75] Inventors: Tsumoru Renge, Hyogo; Osamu Yamada, Hasaki; Katumi Omura, Kamisu, all of Japan

[73] Assignee: Kuraray Co., Ltd., Kurashiki, Japan

[21] Appl. No.: 422,049

[22] Filed: Oct. 16, 1989

[30] Foreign Application Priority Data

Oct. 26, 1988 [JP] Japan .................. 63-271452

[51] Int. Cl.$^5$ .................................. C07L 29/60
[52] U.S. Cl. .................... 568/903; 568/857; 568/698
[58] Field of Search .............. 568/903, 698, 857

[56] References Cited

U.S. PATENT DOCUMENTS 3,966,829 6/1976 Engelhardt et al. ............... 568/903

Primary Examiner—Howard T. Mars
Attorney, Agent, or Firm—Oblon, Spivak, McClelland, Maier & Neustadt

[57] ABSTRACT

A process for producing homoallyl alcohols of the general formula (I)

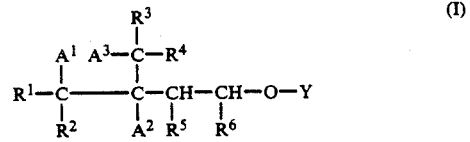

in which either $A^1$ or $A^3$ represents a hydrogen atom, the other represents a single bonding along with $A^2$; $R^1$, $R^2$, $R^3$, $R^4$, $R^5$ and $R^6$ are the same or different and independently represents a hydrogen atom, or an alkyl or alkenyl group with or without being substituted with a hydroxyl group or an akoxyl group; and Y represents a hydrogen atom, an alkyl group or an alkenyl group, by reacting 1,3-glycols of the general formula (II)

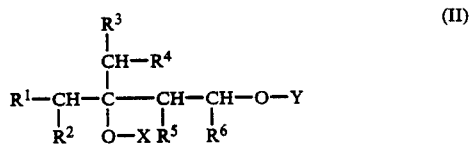

in which X and Y are the same or different and independently represents a hydrogen atom, an alkyl group or an alkenyl group, $R^1$, $R^2$, $R^3$, $R^4$, and $R^5$ independently represents as defined above, at a temperature in the range of 130° to 250° C. in liquid phase with the contact of γ-alumina catalyst.

11 Claims, No Drawings

PROCESS FOR PRODUCING HOMOALLYL ALCOHOLS

BACKGROUND OF THE INVENTION

1. Field of the Invention

This invention relates to a process for producing homoallyl alcohols of the following formula (I)

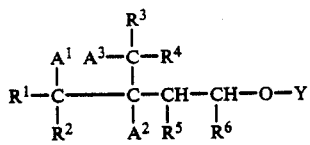

in which either $A^1$ or $A^3$ represents a hydrogen atom, the other represents a single bonding along with $A^2$; $R^1$, $R^2$, $R^3$, $R^4$, $R^5$ and $R^6$ are the same or different and independently represents a hydrogen atom, or an alkyl or alkenyl group with or without being substituted with an hydroxyl group or an alkoxyl group; and Y represents a hydrogen atom, an alkyl group or an alkenyl group.

Homoallyl alcohols of the general formula (I) produced according to the present invention are useful as starting material for producing fragrance chemicals, pharmaceuticals and agricultural chemicals.

2. Description of the Prior Art

Homoallyl alcohols are known as prepared according to the following processes.

A process consisting of dehydration of 3-methyl-1,3-butanediol under heating in the presence of phosphoric acid or iodine gives 3-methyl-3-butene-1-ol with a yield of 35% and isoprene with a yield of 30–35% (Bulletin de la Societe Chimique de France 1964 pp800–804).

A process of catalytic dehydration of 3-methyl-1,3-butanediol in the presence of alumina catalyst, silica-alumina catalyst or calcium phosphate catalyst gives 3-methyl-3-butene-1-ol and 3-methyl-2-butene-1-ol with a maximum combined yield of 50% (Neftekhimiya 3, No. 1, 104–107 (1963)).

These prior art processes have problems from the standpoint of industrial production. That is, raising the conversion ratio of 3-methyl-1,3-butanediol to a satisfactory level for the standpoint of industrial production reduces the yield of 3-methyl-3-butene-1-ol because of the inevitable formation of isoprene.

If phosphoric acid is used for catalyst, inevitable using of equipments made of high corrosion-resistant metals because of corrosive properties of phosphoric acid to metals, makes the facility cost too expensive.

If iodine is used for catalyst, higher cost of iodine is disadvantageous for the process. Also, iodine tends to contaminate the product because of its volatility, which makes its removal essential, and the manufacturing process becomes unpreferably complex.

The method shown in Neftekhimyka 3, No. 1 104–107 (1963) has further a problem that the hourly formed amount of the compound of the general formula (I) per unit volume of catalyst is low while keeping the selectivity ratio at an adequate level.

SUMMARY OF THE INVENTION

An object of the invention is to provide an industrially advantageous process for producing homoallyl alcohols of the general formula (I) with high selectivity, in high hourly formed amount per catalyst weight and inexpensively.

According to the present invention, there is provided a process of the dehydration of 1,3-glycols of the general formula (II)

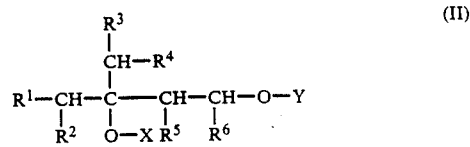

in which $R^1$, $R^2$, $R^3$, $R^4$, $R^5$ and $R^6$ are the same or different and independently represents a hydrogen atom, or an alkyl or alkenyl group with or without being substituted with a hydroxyl group or an alkoxyl group, and X and Y are the same or different and independently represents a hydrogen atom, an alkyl group or an alkenyl group, characterized in:

(a) that the reaction is carried out in the presence of γ-alumina catalyst;

(b) that the homoallyl alcohols of the general formula (I) and the compounds of the general formula (III)

$$X-OH \qquad (III)$$

in which X represents as defined above, are distilled off from the reaction zone during the reaction;

(c) that the temperature of the reaction zone is 130°–250° C.

According to the process of the present invention, homoallyl alcohols of the general formula (I) can be produced in high selectivity ratio and in high hourly formed amount per catalyst weight, and also inexpensively on account of being able to maintain high catalyst activity.

DESCRIPTION OF THE PREFERRED EMBODIMENT $R^1$, $R^2$, $R^3$, $R^4$, $R^5$, $R^6$, X and Y in the above general formulae will be described more particularly.

$R^1$, $R^2$, $R^3$, $R^4$, $R^5$ and $R^6$ are the same or different, and independently represents a hydrogen atom or an alkyl or alkenyl group with or without being substituted with a hydroxyl group or an alkoxyl group.

Examples of the alkyl group include a methyl group, an ethyl group, a propyl group, an isopropyl group, a butyl group and the like. The alkyl group may be substituted with a hydroxyl group or alkoxyl group such as a methoxy group, an ethoxy group, a propoxy group, an isopropoxy group and a butoxy group.

Examples of the alkyl group substituted with a hydroxyl group include a hydroxymethyl group, a 1-hydroxyethyl group, a 2-hydroxyethyl group and the like; and that of the alkyl group substituted with an alkoxyl group include a methoxymethyl group, an ethoxymethyl group, a 1-methoxyethyl group, a 2-methoxyethyl group and the like.

Examples of the alkenyl group include a vinyl group, an allyl group, a 1-propenyl group, an isopropenyl group, a 1-butenyl group, a 2-butenyl group, a 3-butenyl group, a 3-methyl-2-butenyl group, a 3-methyl-3-butenyl group and the like.

As described above, X and Y are the same or different and independently represents a hydrogen atom, an alkyl group or an alkenyl group.

Examples of the alkyl group include a methyl group, an ethyl group, a propyl group, an isopropyl group, a butyl group, a pentyl group, a isopentyl group, a tert-pentyl group and the like, and that of the alkenyl group include a vinyl group, an allyl group, a 1-propenyl group, an isopropenyl group, a 1-butenyl group, a 2-butenyl group, a 3-butenyl group, a 3-methyl-2-butenyl group, a 3-methyl-3-butenyl group and the like.

The process according to the present invention can be effected as liquid-phase reaction in a continuous process or a batchwise process.

The γ-alumina used for the present invention has an effect that the larger the pore volume of alumina, the faster the reaction rate; and the smaller the pore volume of alumina, the higher the selectivity for homoallyl alcohols of the general formula (I). From these results, preferably, the pore-size of alumina is in the range of 16–330 Å and the pore volume of alumina with said pore-size is in the range of 0.1–1.0 cc/g.

For the reaction of the invention, industrial γ-aluminas with a usual purity, such as having a water content of not more than about 10% by weight, a silica content of not more than about 1% by weight, an iron oxide content of not more than about 1% by weight, an alkali metal oxide content of not more than about 1% by weight, an alkali earth metal oxide content of not more than about 1% by weight and a sulfate content of not more than about 0.5% by weight may be used, but preferably having an alkali metal oxide and an alkali earth metal oxide content of not more than 0.3% by weight from the standpoint of having sufficiently higher reaction rate.

The amount of γ-alumina used for the reaction is normally about 2–100% by weight per the hourly feed amount of 1,3-glycols of the general formula (II) and preferably about 5–30% by weight.

There is no limitation to the form of γ-alumina and any forms of alumina, such as powder, pellet, extrusion molded and the like can be used.

The reaction according to the present invention can be effected with an organic solvent having a boiling point of higher than the boiling point of both homoallyl alcohols of the general formula (I) and the compounds of the general formula (III), and having no adverse effects on the reaction.

Examples of such solvents include hydrocarbons with a higher boiling point such as liquid paraffin, squalane and the like, and polyether polyols such as oligomers and polymers of ethylene glycol, propylene glycol and 1,4-butanediol and the like, and also 1,3-glycols of the general formula (II) can serve as the solvent.

The reaction according to the present invention is conducted at a temperature in the range of 130°–250° C., preferably in the range of 150°–210° C. If the reaction temperature is lower than 130° C., the reaction rate can not be adequate level, and if it is higher than 250° C., the loss of homoallyl alcohols due to thermal decomposition increases remarkably.

The reaction according to the present invention is carried out at normal pressure, reduced pressure or under pressure to become the reaction temperature in the range of 130°–250° C. considering the boiling points of 1,3-glycols of the general formula (II) and homoallyl alcohols of the general formula (I). The reaction pressure is usually in the range of 0.01–20 kg/cm² (absolute pressure) and preferably in the range of 0.05–10 kg/cm² (absolute pressure).

Generally, in case of using a solid catalyst, such as γ-alumina, by-produced tar-like substances and the like may reduce catalyst activity, but in the process according to the present invention, marked inhibition of catalyst activity occurs very rarely so that stable reaction can be run for a long period.

The homoallyl alcohols of the general formula (I) according to the present invention can be obtained from the distillate from the reaction system by a common separation operation such as distillation or the like.

The 1,3-glycols of the general formula (II) used in the present invention may be readily prepared by the reaction of olefins of the general formula (IV)

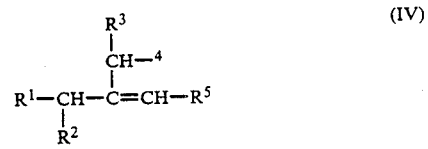

in which $R^1$, $R^2$, $R^3$, $R^4$ and $R^5$ independently represents as defined above and formaldehyde in the presence of acid catalyst, or the hydrolysis or alcoholysis of 1,3-dioxanes of the general formula (V)

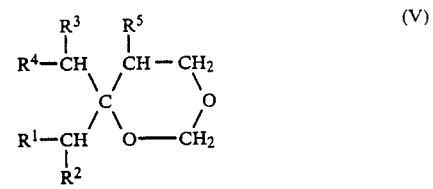

in which $R^1$, $R^2$, $R^3$, $R^4$ and $R^5$ independently represents as defined above, simultaneously obained in the former reaction in the presence of acid catalyst.

Further this compound can be readily obtained by the hydrogenation of ketoalcohols of the general formula (VII)

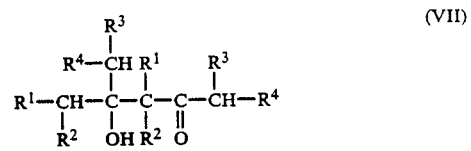

in which $R^1$, $R^2$, $R^3$ and $R^4$ independently represents as defined above, obtained by condensing ketones of the general formula (VI)

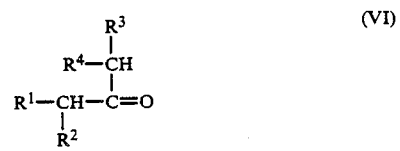

in which $R^1$, $R^2$, $R^3$ and $R^4$ independently represents as defined above in the presence of alkali catalyst, or the hydrogenation of ketoalcohols of the general formula (VIII)

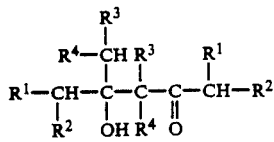

(VIII)

in which $R^1$, $R^2$, $R^3$ and $R^4$ independently represents as defined above.

The present invention is more particularly described by way of examples, which should not be construed as limiting the present invention.

EXAMPLE 1

In a 300 ml capacity glass autoclave equipped with a thermometer, a stirrer, a feed opening and a distillation opening fitted with a reflux condenser and a MacMahon packed column having an inner diameter of 10 mm and a length of 150 mm and connected with a dry ice-acetone trap, 300 g of 3-methyl-1,3-butanediol and 60 g of powdered γ-alumina (prepared by grounding alumina catalyst N-611-N made by Nikki Chemical Co., Ltd. and passing through 150 mesh sieve and having a pore volume of 0.33 cc/g with a pore size in diameter in the range of 16–330 A) were placed, and the inner atmosphere was replaced with nitrogen gas.

The suspension had been heated at atmospheric pressure with stirring, and the feed of 3-methyl-1,3-butanediol was started at a feed rate of 180 g/hr. At the time when the temperature of the reaction zone reached at 188° C., the collection of the distillate was started by opening the distillation opening. The suspension in the autoclave had been kept at a constant volume by regulating the amount of heat from heater. And also the temperature of the reaction zone was kept at 188° C.

In 5 hours from starting to feed 3-methyl-1,3-butanediol and to collect the distillate, 900 g of distillate was obtained. The gas chromatography analysis of the distillate revealed that the distillate contained 61.2 g of unreacted 3-methyl-1,3-butanediol (conversion ratio of 3-methyl-1,3-butanediol: 93.2%) and 590.3 g of 3-methyl-3-butene-1-ol (selectivity ratio of 3-methyl-3-butene-1-ol: 85.1 mole%, hourly formed amount per catalyst weight: 1.97 g/g.hr). Water in the distillate was 145.2 g.

EXAMPLE 2

The reaction was carried out under the same conditions as Example 1 except that, there was used, instead of 300 g of 3-methyl-1,3-butanediol, 300 g of liquid paraffin, thereby obtaining 900 g of distillate.

The distillate contained 173.7 g of unreacted 3-methyl-1,3-butanediol (conversion ratio of 3-methyl-1,3-butanediol: 80.7%) and 514.7 g of 3-methyl-3-butene-1-ol (selectivity ratio of 3-methyl-3-butene-1-ol: 85.7 mole%, hourly formed amount per catalyst weight: 1.72 g/g.hr). Water in the distillate was 125.7 g.

EXAMPLE 3–15

The reaction was carried out under the same conditions as Example 1 except that, there was used, instead of 300 g of 3-methyl-1,3-butanediol, 300 g of 1,3-glycols having the substituted group indicated in Table 1, at the feed rate, reaction temperature and reaction pressure indicated in Table 1, thereby obtaining the corresponding homoallyl alcohols of the general formula (I). The results are shown in Table 1.

TABLE 1

| Example | \multicolumn{8}{c}{1,3-Glycols of the General Formula (II) Substituted Group} | Feed Rate (g/hr) | Reaction Temperature (°C.) |
|---|---|---|---|---|---|---|---|---|---|---|
| | $R^1$ | $R^2$ | $R^3$ | $R^4$ | $R^5$ | $R^6$ | X | Y | | |
| 3 | H | H | H | H | $CH_3$ | H | H | H | 150 | 191 |
| 4 | H | H | H | H | H | $CH_3$ | H | H | 150 | 190 |
| 5 | H | H | H | H | H | H | $CH_3$ | H | 50 | 180 |
| 6 | H | H | H | H | H | H | H | $CH_3$ | 100 | 195 |
| 7 | H | H | H | H | H | H | $CH_3$ | $CH_3$ | 50 | 198 |
| 8 | H | H | H | H | $HOCH_2-$ | H | H | H | 100 | 210 |
| 9 | $HOCH_2-$ | H | H | H | H | H | H | H | 100 | 220 |
| 10 | $CH_3$ | H | $CH_3$ | H | H | H | H | H | 100 | 198 |
| 11 | H | H | H | H | H | H | $(CH_3)_2C=CHCH_2-$ | H | 100 | 202 |
| 12 | H | H | H | H | H | H | H | $(CH_3)_2C=CHCH_2-$ | 100 | 202 |
| 13 | $CH_2=CCH_2CH_2-$ ( $CH_3$ branch) | H | H | H | H | H | H | H | 100 | 225 |
| 14 | $CH_3OCH_2-$ | H | H | H | H | H | $CH_3$ | H | 100 | 205 |
| 15 | $CH_3$ | Me | H | H | H | H | H | H | 100 | 210 |

| Example | Reaction pressure (kg/cm²)[1] | Distillate Total Weight (g) | Weight of Unreacted 1,3-Glycols (g) | Weight of Homoallyl Alcohols (g) | Weight of X—OH (g) | Conversion ratio of 1,3-Glycols (%) | Selectivity ratio of Homoallyl Alcohols (mole %) | Hourly formed amount per catalyst weight (g/g · hr) |
|---|---|---|---|---|---|---|---|---|
| 3 | 1.0 | 750 | 51.0 | 501.7 | 106.6 | 93.2 | 84.7 | 1.67 |
| 4 | 1.0 | 750 | 65.3 | 482.8 | 104.5 | 91.3 | 83.2 | 1.61 |
| 5 | 3.0 | 250 | 16.5 | 131.2 | 63.3 | 93.4 | 77.1 | 0.44 |
| 6 | 4.5 | 500 | 52.5 | 379.2 | 68.3 | 89.5 | 78.8 | 1.26 |
| 7 | 3.5 | 250 | 29.5 | 167.0 | 53.5 | 88.2 | 71.3 | 0.57 |
| 8 | 0.05 | 500 | 37.5 | 318.3 | 62.1 | 92.5 | 79.5 | 1.06 |
| 9 | 0.05 | 500 | 36.5 | 338.6 | 62.3 | 92.7 | 84.4 | 1.13 |
| 10 | 1.0 | 500 | 34.5 | 329.7 | 63.5 | 93.1 | 82.0 | 1.10 |
| 11 | 1.0 | 500 | 29.0 | 183.0 | 235.5 | 94.2 | 77.7 | 0.61 |
| 12 | 0.1 | 500 | 22.5 | 344.7 | 50.5 | 96.5 | 79.8 | 1.15 |
| 13 | 0.05 | 500 | 38.5 | 312.4 | 48.3 | 92.3 | 75.6 | 1.04 |
| 14 | 0.05 | 500 | 35.0 | 269.4 | 91.9 | 93.0 | 72.2 | 0.90 |

TABLE 1-continued

| 15 | 1.0 | 500 | 11.5 | 322.7 | 66.6 | 97.7 | 76.5 | 1.08 |

EXAMPLES 16-19

The reaction was carried out under the same conditions as Example 1 except that, there was used, instead of 60 g of γ-alumina and 180 g/hr of feed rate of 3-methyl-1,3-butanediol, the amount of γ-alumina and the feed rate of 3-methyl-1,3-butanediol indicated in Table 2, thereby obtaining the results indicated in Table 2.

N-611-N made by Nikki Chemical Co., Ltd), thereby obtaining 900 g of distillate.

The distillate was found containing 117 g of unreacted 3-methyl-1,3-butanediol (conversion ratio of 3-methyl-1,3-butanediol: 87.0%) and 519.3 g of 3-methyl-3-butene-1-ol (selectivity ratio of 3-methyl-3-butene-1-ol: 80.2 mole%, hourly formed amount per catalyst weight: 1.73 g/g.hr). Water in the distillate was 135.5 g.

TABLE 2

| Example | Amount of γ-Alumina used (g) | Feed rate of 3-Methyl-1,3-butanediol (g/hr) | Distillate Total Wt. (g) | Wt. of Unreacted 3-Methyl-1,3-butanediol (g) | Wt. of 3-Methyl-3-butene-1-ol (g) | Wt. of Water (g) | Conversion ratio of 3-Methyl-1,3-butanediol (%) | Selectivity ratio of 3-Methyl-3-butene-1-ol (mole %) | Hourly formed amount per catalyst weight (g/g · hr) |
|---|---|---|---|---|---|---|---|---|---|
| 16 | 60 | 150 | 750 | 71.3 | 480.5 | 117.5 | 90.5 | 85.6 | 1.60 |
| 17 | 30 | 105 | 525 | 44.6 | 341.6 | 83.1 | 91.5 | 86.0 | 2.28 |
| 18 | 15 | 75 | 375 | 29.3 | 249.0 | 59.8 | 92.2 | 87.1 | 3.32 |
| 19 | 4 | 38 | 190 | 12.2 | 132.1 | 30.8 | 93.6 | 89.8 | 6.61 |

EXAMPLES 20-22

The reaction was carried out under the same conditions as Example 1 except that, there was used, instead of 60 g of powdered γ-alumina passed through 150 mesh sieve, powdered γ-alumina indicated in Table 3, thereby obtaining the results indicated in Table 3.

EXAMPLE 24

The reaction was carried out under the same conditions as Example 1 except that, there were conducted, instead of one sampling of 900 g of the distillate for 5 hours, repeated samplings for 5 hours, at 24-hr intervals, thereby obtaining the results indicated in Table 4.

TABLE 3

| Example | Powdered Alumina Form of Alumina | Pore Volume[1] (cc/g) | Cont. of sodium oxide[2] (g/g — Al₂O₃) | Distillate Total Wt. (g) | Wt. of Unreacted 3-Methyl-1,3-butanediol (g) | Wt. of 3-Methyl-3-butene-1-ol (g) | Wt. of Water (g) | Conversion ratio of 3-Methyl-1,3-butanediol (%) | Selectivity ratio of 3-Methyl-3-butene-1-ol (mole %) | Hourly formed amount per catalyst weight (g/g · hr) |
|---|---|---|---|---|---|---|---|---|---|---|
| 20 | γ-Alumina | 0.48 | 0.0001 | 900 | 76.5 | 578.8 | 142.5 | 91.5 | 85.0 | 1.61 |
| 21 | γ-Alumina | 0.53 | 0.0010 | 900 | 106.2 | 559.3 | 137.4 | 88.2 | 85.2 | 1.55 |
| 22 | γ-Alumina | 0.49 | 0.00005 | 900 | 67.5 | 586.5 | 144.1 | 92.5 | 85.2 | 1.63 |

Notes:
[1] Pore volume with a pore size in diameter of 16-300 Å
[2] Weight ratio of sodium oxide to $Al_2O_3$

TABLE 4

| Sampling time from start (hr) | Reaction temperature (°C.) | Conversion ratio of 3-methyl-1,3-butanediol (%) | Selectivity ratio of 3-methyl-3-butene-1-ol (%) | Hourly formed amount per catalyst weight (g/g · hr) |
|---|---|---|---|---|
| 1-6 | 188 ± 2 | 93.8 | 84.8 | 1.98 |
| 25-30 | 188 ± 1 | 92.6 | 87.0 | 2.00 |
| 49-54 | 188 ± 2 | 93.5 | 85.2 | 1.98 |
| 73-78 | 188 ± 2 | 91.9 | 86.0 | 1.96 |
| 97-102 | 188 ± 1 | 92.3 | 84.2 | 1.93 |
| 121-126 | 188 ± 2 | 93.2 | 83.0 | 1.92 |
| 145-150 | 188 ± 2 | 92.5 | 84.1 | 1.93 |
| 169-174 | 188 ± 2 | 93.4 | 83.2 | 1.93 |
| 193-198 | 188 ± 1 | 91.8 | 83.7 | 1.91 |
| 217-222 | 188 ± 2 | 92.9 | 85.1 | 1.96 |
| 241-246 | 188 ± 2 | 93.6 | 82.5 | 1.92 |
| 265-270 | 188 ± 1 | 93.0 | 83.3 | 1.92 |
| 289-294 | 188 ± 2 | 93.7 | 83.6 | 1.95 |

EXAMPLE 23

The reaction was carried out under the same conditions as Example 1 except that, there were used, instead of powdered γ-alumina, pelletized γ-alumina (prepared by pelletized in 5 mm φ×5 mm of alumina catalyst

What is claimed is:

1. A process for producing homoallyl alcohols of the general formula (I)

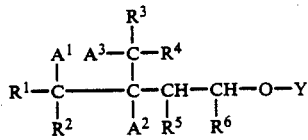 (I)

in which either $A^1$ or $A^3$ represents a hydrogen atom, the other represents a single bonding along with $A^2$; $R^1$, $R^2$, $R^3$, $R^4$, $R^5$ and $R^6$ are the same or different and independently represents a hydrogen atom, or an alkyl or alkenyl group with or without being substituted with an hydroxyl group or an alkoxyl group; and Y represents a hydrogen atom, an alkyl group or an alkenyl group, by the dehydration of 1,3-glycols of the general formula (II)

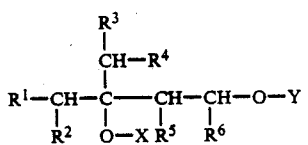 (II)

in which $R^1$, $R^2$, $R^3$, $R^4$, $R^5$ and $R^6$ independently represents as defined above, and X and Y are the same or different and independently represents a hydrogen atom, an alkyl group or an alkenyl group, characterized in:

(a) that the reaction is carried out in the presence of γ-alumina catalyst;

(b) that the homoallyl alcohols of the general formula (I) and the compounds of the general formula (III)

$$X\text{—}OH \quad (III)$$

in which X represents as defined above, are distilled off from the reaction zone during the reaction;

(c) that the temperature of the reaction zone is 130°–250° C.

2. The process according to claim 1, wherein $R^1$, $R^2$, $R^3$ and $R^4$ in said formulae (I) and (II) are hydrogen atom.

3. The process of claim 2, wherein $R^1$, $R^2$, $R^3$, $R^4$, $R^5$, and $R^6$ in the formulae (I) and (II) are hydrogen atom.

4. The process of claim 1, wherein X in the formulae (II) and (III) is hydrogen atom or methyl group.

5. The process of claim 1, wherein Y in the formulae (I) and (II) is hydrogen or methyl group.

6. The process of claim 1, wherein 1,3-glycol of the general formula (II) is 3-methyl-1,3-butanediol.

7. The process of claim 1, wherein the temperature of the reaction zone is 150°–210° C.

8. The process of claim 1, wherein the pore size of the γ-alumina is in the range of 16–330 Å.

9. The process of claim 1, wherein the pore volume of the γ-alumina is in the range of 0.1–1.0 cc/g.

10. The process of claim 1, wherein the amount of γ-alumina is 2–100% by weight per the hourly feed amount of 1,3-glycol.

11. The process of claim 1, wherein the amount of γ-alumina is 5–30% by weight per the hourly feed amount of 1,3-glycol.

* * * * *